(12) United States Patent
Kennedy et al.

(10) Patent No.: US 7,815,859 B2
(45) Date of Patent: Oct. 19, 2010

(54) METHOD AND APPARATUS FOR DETERMINING THE OXYGEN PERMEABILITY OF A POLYMER MEMBRANE

(75) Inventors: Joseph P. Kennedy, Akron, OH (US); Gabor Erdodi, Akron, OH (US)

(73) Assignee: The University of Akron, Akron, OH (US)

( * ) Notice: Subject to any disclaimer, the term of this patent is extended or adjusted under 35 U.S.C. 154(b) by 454 days.

(21) Appl. No.: 11/815,489

(22) PCT Filed: Feb. 24, 2006

(86) PCT No.: PCT/US2006/006499

§ 371 (c)(1),
(2), (4) Date: Mar. 31, 2008

(87) PCT Pub. No.: WO2006/093818

PCT Pub. Date: Sep. 8, 2006

(65) Prior Publication Data

US 2008/0233006 A1    Sep. 25, 2008

Related U.S. Application Data

(60) Provisional application No. 60/656,309, filed on Feb. 25, 2005.

(51) Int. Cl.
    *G01N 15/08*      (2006.01)
    *G01N 33/00*      (2006.01)
    *G01N 15/06*      (2006.01)
(52) U.S. Cl. .................. 422/68.1; 73/38; 73/64.47; 436/127
(58) Field of Classification Search .................. 73/38
See application file for complete search history.

(56) References Cited

U.S. PATENT DOCUMENTS

| 5,229,465 | A | | 7/1993 | Tsuchida et al. |
| 5,863,460 | A | * | 1/1999 | Slovacek et al. ....... 252/301.35 |
| 6,406,517 | B1 | * | 6/2002 | Avery et al. .................... 95/45 |
| 6,441,055 | B1 | | 8/2002 | Katerkamp et al. |

FOREIGN PATENT DOCUMENTS

WO    WO 2006/093818 A3    9/2006

OTHER PUBLICATIONS

Amatore, C.A. et al, Space variables well fitted for the study of steady state and near-steady-state diffusion at a microdisk, J. Electoanal. Chem. 328, 1992, pp. 21-32.

(Continued)

*Primary Examiner*—Jill Warden
*Assistant Examiner*—Jennifer Wecker
(74) *Attorney, Agent, or Firm*—Joseph J. Crimaldi; Roetzel & Andress

(57) ABSTRACT

The present invention is relates to an apparatus and method for the determination of the oxygen gas permeability of a polymer. In one embodiment, the present invention relates to an apparatus and method for determining the oxygen gas permeability of a polymer membrane (e.g., a polydimethylsiloxane and/or polysiloxane polymer or copolymer). In still another embodiment, the present invention relates to oxygen gas permeable polymer compositions.

40 Claims, 5 Drawing Sheets

OTHER PUBLICATIONS

Galceran, J. et al, Two-dimensional implementation of the finite element method with singularity correction . . . , Journal of Electroanalytical Chemistry 394, 1995, pp. 17-28.

Galceran, J. et al, Analytical solution for the steady-state diffusion towards an inlaid disc microelectrode in . . . , Journal of Electroanalytical Chemistry 440, 1997, pp. 1-25.

Kurian, P. et al, Synthesis, permeability and biocompatibility of tricomponenet membranes containing polyethylene glycol, . . . , Biomaterials 24, 2003, pp. 3493-3503.

Isayeva, I.S. et al, Characterization and performance of membranes designed for macroencapsulation/implantation of pancreatic islet cells, Biomaterials 24, 2003, pp. 3483-3491.

Kurian, P. et al, Novel Cyclosiloxane-based Networks, Polym Prep 2003, 44, pp. 33-34.

Obendorf, D. et al, Determination of Oxygen Permeability/transmissibility and Storage of Contact Lenses Using HPLC with Reductive . . . , Anal. Chem. 2003, 75, pp. 1374-1381.

Kurian, P. et al, Poly(pentamethylcyclopentasiloxane). I. Synthesis and Characterization, J. of Polym. Sci. Polym. Chem. 2002, 40, pp. 1285-1292.

International Standard ISO 9913-1: 1196(E), Optics and Optical Instruments-Contact Lenses-Part 1: Determination of Oxygen Permeability and Transmissiblity by the FATT method.

Alvord, L. et al, Oxygen Permeability of a New Type of High Dk Soft Contact Lens Material, Optometry and Vision Science 1998, 75, No. 1, pp. 30-36.

Stern, S.A., Polymers for gas separations: the next decade, Journal of Membrane Science 1994, 94, pp. 1-65.

Koros, W.J. et al, Material Selection Considerations for Gas Separation Processes, Polymer Engineering and Science 1987, 27, No. 8, pp. 603-610.

Sereda, L. et al, Influence of silica and black rice husk ash fillers on the diffusivity and solubility of gases in silicone rubbers, Polymer 44, 2003, pp. 3085-3093.

Koros, W.J. et al, Polymeric Membrane Materials for Solution-Diffusion Based Permeation Separations, Prog. Polym. Sci. 1998, 13, pp. 339-401A guy walks into a post office one.

Stern, S.A. et al, Structure-Permeability Relationship in Silicone Polymers, Journal of Polymer Science: Part B: Polymer Physics 1987, 25, pp. 1263-1298.

Merkel, T.C. et al, Gas Sorption, Diffusion, and Permeation in Poly(dimethylsiloxane), Journal of Polymer Sceince: Part B: Polymer Physics 2000, 38, pp. 415-434.

Compan, V. et al, Permeability and Diffusional Studies on Silicone Polymer Networks with Controlled Dangling Chains, Polymer 1996, 37, No. 1, pp. 101-107.

Weissman, B.A. et al, Polarographic Oxygen Permeability Measurement of Silicone Elastomer Contact Lens Material, J AM Optom Assoc 1992, 63(3), pp. 187-190.

Sweeney, D., Silicone Hydrogels: the rebirth of continuous wear contact lenses, Oxford: Butterworth-Heinemann 2000.

Comyn, J. et al, Polymer permeability, Elsevier Applied Science: London 1986.

Hitchman, M.L., Measurement of dissolved oxygen, Wiley, New York 1985.

Gnaiger, E. et al, Polarographic Oxygen Sensors, Springer, Berlin 1983.

* cited by examiner

METHOD AND APPARATUS FOR DETERMINING THE OXYGEN PERMEABILITY OF A POLYMER MEMBRANE

FIELD OF INVENTION

The present invention is relates to an apparatus and method for the determination of the oxygen gas permeability of a polymer. In one embodiment, the present invention relates to an apparatus and method for determining the oxygen gas permeability of a polymer membrane (e.g., a polydimethylsiloxane and/or polysiloxane polymer or copolymer). In still another embodiment, the present invention relates to oxygen gas permeable polymer compositions.

BACKGROUND OF THE INVENTION

Oxygen permeability is one of the main weaknesses for the clinical application of biological hydrogel membranes, e.g., immunoisolatory membranes, extended-wear soft contact lenses. Investigations on novel fully synthetic membranes for biomedical applications, including extended wear soft contact lenses, necessitate the determination of the oxygen permeabilities of water swollen membranes rapidly, precisely and reproducibly. Pertinent literature reveals that the required methodology for the determination of high (Dk>100 barrers) oxygen permeability water-swollen hydrogels is unavailable or fraught with other issues.

One method for determining the oxygen permeability of water-swollen hydrogels is the Fatt method (International Standard ISO 9913-1: 1996(E)). However, this analytical technique is only reliable in the Dk equal to the 1 to 100 barrer range. Given the above this technique is inadequate to provide accurate values for highly oxygen permeable silicon-based contact lenses, such as lotrafilcon (Dk=140 barrers) and balafilcon (Dk=110 barrers). The Fatt method is unsuitable for the determination of high oxygen permeabilities because of insufficient understanding of the electrode/polymer (solid/solid) interface and unpredictable edge effects at higher permeabilities.

Since the introduction of modern silicon-based hydrogels for extended-wear soft contact lenses in 1997 several attempts have been made to develop techniques for the measurement of oxygen permeabilities above the 100 barrer value. A methodology has been developed in which the oxygen permeability of water-swollen soft contact lenses placed between two diffusion chambers is determined by the use of a chromatographic oxygen sensor. The detector used for the determination of oxygen concentration is part of a HPLC (High Performance Liquid Chromatography) system and samples are taken from the diffusion chambers and injected into the HPLC. One advantage of this methodology is that the analyzing unit is isolated from the diffusion chambers and hence is independent from the measurement conditions. The oxygen sensor is capable of detecting oxygen in the range of 0.01 mg/L to 10.0 mg/L. The reproducibility and the reported error for both low and high oxygen permeability contact lenses were quite low (6 to 10%). However, the Dk values for the high permeability lenses had a 20 to 30% error margin when compared to the values claimed by the manufacturers and those determined by other suitable testing methods. Although the above method claims steady state conditions are not needed for accurate measurements, the equations used in this method presume such conditions. Also, this method utilizes a water phase HPLC system, and such an HPLC system and a detector having the necessary sensitivity are expensive, thereby limiting the use of this technique.

Alvord et al. (Optometry & Vision Science, 1998, 75(1), pp. 30 to 36) determined the oxygen permeability (Dk) and transmissibility (Dk/l) of lotrafilcon A lenses by a modified standard coulometric method. The coulometric method is the ISO standard for measuring the oxygen permeability of rigid contact lenses but cannot be used for soft contact lenses. Contact lenses with different thicknesses were measured in liquid-to-gas and gas-to-gas configurations in an effort to combine the features of the Fatt method with the advantages of the coulometric method. Oxygen permeabilities were measured with the same or less error than the Fatt method is capable of and the results were within 10% of the nominal values with low relative errors. Although this method is theoretically suitable for the determination of oxygen permeabilities with Dk values of 200 or more barrers, there is no concrete evidence that such measurements are in fact accurate.

If it were possible to determine oxygen permeability values above a Dk of 200 or more barrers, another possible problem with the Alvord test is that the Alvord test may yield data that is unreliable due to a failure to properly account for the edge effect and boundary layer effect.

PDMS (polydimethylsiloxane) occupies a special position among highly oxygen permeable materials. It has by far the highest oxygen permeability (Dk value) among rubbers and has the second highest Dk among all polymers (currently the highest Dk of all polymeric materials is exhibited by poly[1-(trimethylsilyl)-1-propyne]). The oxygen permeability of PDMS is typically determined in the dry state using a well-known method for the testing of gas separation membranes. According to various literature sources the oxygen permeability of unfilled dry PDMS is in the Dk equal to the 700 to 900 barrer range. The relatively wide range of reported Dk values is due to differences in sample preparation, differences in the relative crosslink densities of the test pieces, extrapolation from filled PDMS to unfilled PDMS, presence of impurities, etc, but not to measurement conditions. In spite of the Dk equal to the 700 to 900 barrer range reported for PDMS, most contact lens literature gives Dk's in a significantly lower 200 to 600 barrer range.

There is a need in the art for a technique by which to determine the oxygen permeable values for highly oxygen permeable water-swollen hydrogels (e.g., PDMS containing polymer membranes).

SUMMARY OF THE INVENTION

The present invention is relates to an apparatus and method for the determination of the oxygen gas permeability of a polymer. In one embodiment, the present invention relates to an apparatus and method for determining the oxygen gas permeability of a polymer membrane (e.g., a polydimethylsiloxane and/or polysiloxane polymer or copolymer). In still another embodiment, the present invention relates to oxygen gas permeable polymer compositions.

In one embodiment, the present invention relates to an apparatus for measuring the oxygen gas permeability of a polymer membrane, the apparatus comprising: (a) an oxygen-donating enclosure, where the oxygen-donating enclosure is designed to hold a first gas-enriched liquid, and where the first gas-enriched liquid has a first oxygen gas concentration; (b) an oxygen-receiving enclosure operatively coupled to the oxygen-donating enclosure, where the oxygen-receiving chamber is designed to hold a second gas-enriched liquid, and where the second gas-enriched liquid has a second oxygen gas concentration, the second oxygen gas concentration being at least about 5.0 mg/L less than the first oxygen gas concentration; (c) a polymer membrane holding means, where the polymer membrane holding means is in fluid communication with both the oxygen-receiving enclosure and the oxygen-donating enclosure, where the polymer membrane holding is being designed to prevent liquid mixing of the first and second gas-enriched liquids when a polymer membrane is present in the polymer membrane holding means; (d) a sensor means, where the sensor means monitors the oxygen level present in the oxygen-receiving enclosure; (e) a means for measuring the oxygen gas transport across the polymer membrane and generating oxygen gas transport data therefrom; and (f) a means for determining the oxygen gas permeability of the polymer membrane, where the means for determining the oxygen gas permeability of the polymer membrane involves using the oxygen gas transport data to determine the oxygen permeability of the polymer membrane.

In another embodiment, the present invention relates to a method for determining the oxygen gas permeability of a polymer membrane, the method comprising the steps of: (1) placing a polymer membrane to be tested in a device comprising: (a) an oxygen-donating enclosure, where the oxygen-donating enclosure is designed to hold a first gas-enriched liquid, and where the first gas-enriched liquid has a first oxygen gas concentration; (b) an oxygen-receiving enclosure operatively coupled to the oxygen-donating enclosure, where the oxygen-receiving chamber is designed to hold a second gas-enriched liquid, and where the second gas-enriched liquid has a second oxygen gas concentration, the second oxygen gas concentration being at least about 5.0 mg/L less than the first oxygen gas concentration; (c) a polymer membrane holding means, where the polymer membrane holding means is in fluid communication with both the oxygen-receiving enclosure and the oxygen-donating enclosure, where the polymer membrane holding is being designed to prevent liquid mixing of the first and second gas-enriched liquids when a polymer membrane is present in the polymer membrane holding means; (d) a sensor means, where the sensor means monitors the oxygen level present in the oxygen-receiving enclosure; (e) a means for measuring the oxygen gas transport across the polymer membrane and generating oxygen gas transport data therefrom; and (f) a means for determining the oxygen gas permeability of the polymer membrane, where the means for determining the oxygen gas permeability of the polymer membrane involves using the oxygen gas transport data to determine the oxygen permeability of the polymer membrane; (2) removing any gas bubbles, if present, in the oxygen-receiving enclosure; (3) determining and/or measuring the oxygen consumption rate of the sensor means; (4) determining the initial oxygen concentrations in the oxygen-donating and oxygen-receiving enclosure; and (5) measuring the amount of oxygen gas transport across/through the polymer membrane.

DESCRIPTION OF THE INVENTION

Figure 1:
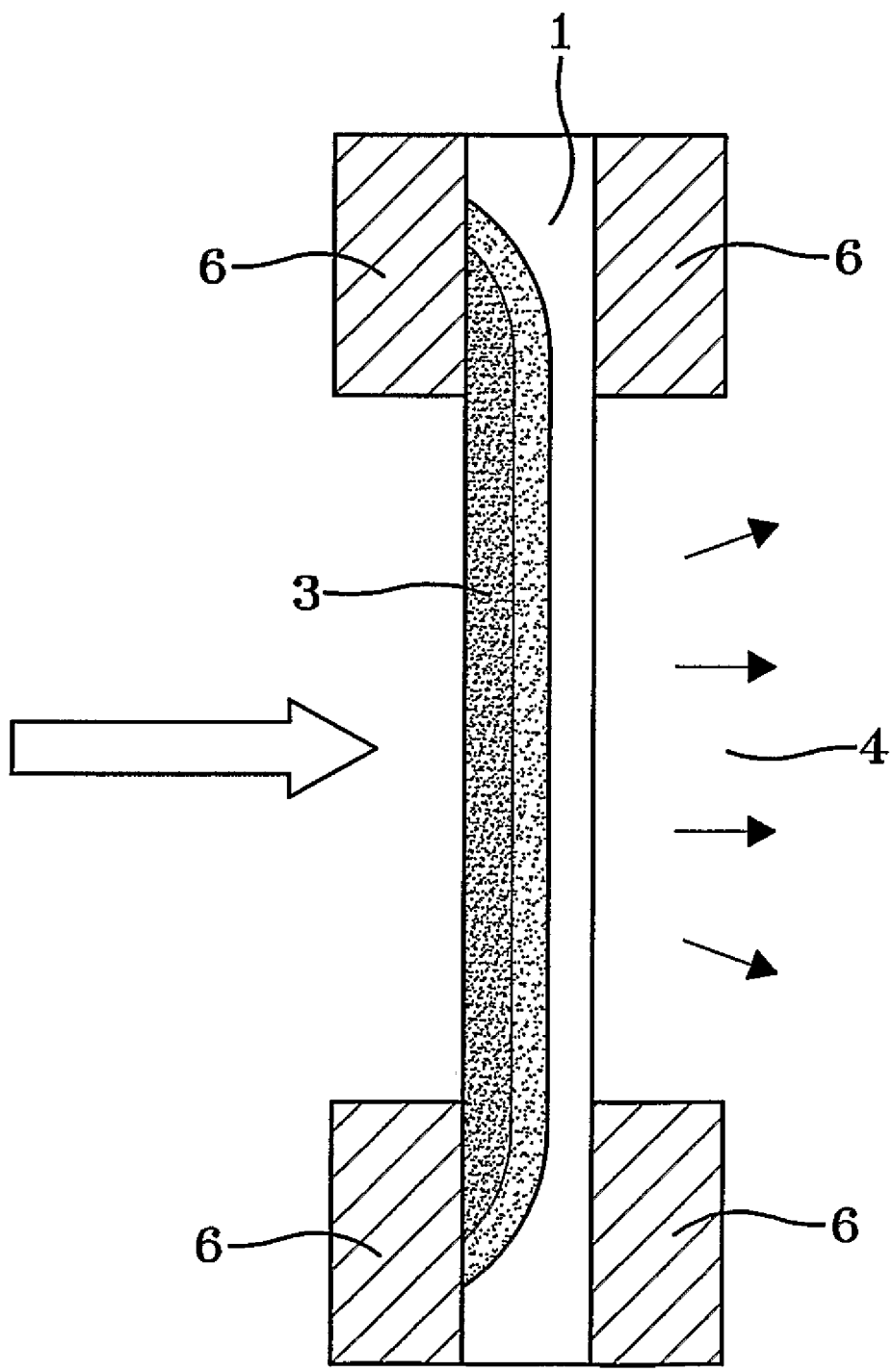
FIG. 1 is a cross-sectional illustration showing a membrane sample and the edge effect of a membrane during a permeability measurement, the concentrations of dissolved oxygen in the phases in contact with the two sides of the membrane, and the higher oxygen concentrations.

The present invention is relates to an apparatus and method for the determination of the oxygen permeability of a polymer. In one embodiment, the present invention relates to an apparatus and method for determining the oxygen permeability of a polymer membrane (e.g., a polydimethylsiloxane and/or polysiloxane polymer or copolymer). In still another embodiment, the present invention relates to oxygen permeable polymer compositions. In yet another embodiment, the present invention enables one to design and/or synthesize highly oxygen permeable polymer membranes.

The present invention is based, in part, on Fick's second law of diffusion. Due to this, the present invention permits the determination of the oxygen permeability of a polymer over a wide range of permeabilities. In one embodiment, the present invention can determine oxygen permeabilities over the range of about 10 to about 5000 barrers, or from about 50 to about 1200 barrers, or from about 100 to about 1000 barrers, or from about 400 to about 900 barrers, or even from about 100 to about 400 barrers. Here, as well as elsewhere in the specification and claims, different range limits can be combined.

Equation (1), as shown below, describes the diffusion of a gas through a membrane and/or polymer membrane that separates two phases with different partial pressures of a gas. The gas flux J, or dn/dt, through the membrane and/or polymer membrane is proportional to the concentration difference of gases ($C_{m1}$–$C_{m2}$) between the two sides of the membrane and/or polymer membrane, the surface of the membrane and/or polymer membrane A, the reciprocal of the membrane and/or polymer membrane thickness l, and the diffusion coefficient D. If the concentration of the gas is expressed by the partial pressures of the gases ($p_1$ and $p_2$), the equation contains the solubility coefficient k which, multiplied by the diffusion constant, gives the permeability coefficient (or permeability for short) Dk as shown below in Equation (1):

$$J = \frac{dn}{dt} = A\frac{D}{l}(C_{m1} - C_{m2}) = A\frac{Dk}{l}(p_1 - p_2). \tag{1}$$

In another embodiment, the present invention involves a method that permits the determination of the oxygen permeability of a polymer membrane and/or polymer film, the method of this embodiment being able to take into account such factors as the boundary layer effect and the edge effect. In still another embodiment, the present invention enables one to determine the oxygen permeability of oxygen permeable waterlogged polymer membranes (e.g., membranes formed from one or more polydimethylsiloxane and polysiloxane polymers or copolymers).

In one instance the present invention can be used to determine the oxygen permeability of polymer membranes formed from polydimethylsiloxane, poly(dimethylsiloxane$_{0.80}$-co-diethylsiloxane$_{0.20}$) or poly(dimethyl-siloxane$_{0.84}$-co-diphenylsiloxane$_{0.16}$). Via the method and apparatus of the present invention, Dk values of 792±26, 505±10 and 249±10 barrers, respectively, are obtained for polymer membranes formed from the above polymer compositions. In light of the oxygen permeability data collected via the method and apparatus of the present invention, it has been determined that the oxygen permeability of a polysiloxane polymer and/or copolymer is diminished by replacing and/or substituting —OSiMe$_2$-repeating unit(s) with —OSiEt$_2$- and/or —OSiPh$_2$- repeating units.

Gas permeability Dk is usually expressed in barrer units, as shown below:

$$\text{barrer} = \frac{[cm^3 STPoxygen][cm]}{[s][cm^2][Hgcm]} 10^{10}$$

It should be noted that Equation (1) is valid only under steady-state conditions, where the concentration profile of the penetrant (e.g., oxygen gas) in the membrane and/or polymer membrane is linear. While the permeability coefficient, or briefly permeability, is a material constant and is independent of membrane thickness; transmissibility, another often used parameter, is permeability divided by membrane and/or polymer membrane thickness: Dk/l.

When a hydrogel membrane is immersed into water during a gas (e.g., oxygen gas) diffusion experiment, a stagnant layer of water is immediately formed at the surface of the membrane that increases the resistance of oxygen flow across the membrane. Due to this stagnant and/or adhering water layer (a.k.a., the "boundary layer"), the oxygen concentration at both surfaces of the membrane will be different from that in the bulk of water. Due to this the so called boundary layer effect, the rate of diffusion of oxygen through the membrane can be significantly lower, particularly in case of highly oxygen permeable membranes (e.g., silicon-based hydrogels).

Equation (2) is a mathematical expression that corrects for the above-described boundary layer effect. The inverse apparent transmissibility of a polymer membrane is the sum of the inverse transmissibilities of the polymer membrane and the aqueous boundary layers. The aqueous boundary layer is expressed as the thickness of the boundary layers $l_{b1}$ and $l_{b2}$ on the two sides of the membrane divided by the oxygen permeability of the boundary layer $Dk_b$:

$$\frac{l}{Dk'} = \frac{l_{b1}}{Dk_b} + \frac{l}{Dk} + \frac{l_{b2}}{Dk_b} \quad (2)$$

During measurement the sample is, in one embodiment, in water and the contribution of the boundary layer to the total resistance is constant, independent of sample thickness; thus Dk can be obtained by determining the apparent permeability (Dk') at several membrane thicknesses and fitting the appropriate function to permeability/thickness data pairs.

The edge effect, common to most diffusion measurements, occurs when the area of a membrane and/or polymer membrane changes as a penetrant (e.g., oxygen gas) passes through the membrane and/or polymer membrane. Due to this geometry, the flow of the penetrant through the membrane and/or polymer membrane becomes non-uniform and a simple Fick equation cannot be used to describe the diffusion process.

FIG. 1 is a cross-sectional illustration showing a membrane and/or polymer membrane 1, held in place by sample holder 6. As shown in FIG. 1, sample holder 6 can be formed from two soft rubber gaskets, although the present invention is not limited thereto. Instead, any suitable structure can be used as sample holder 6, so long as sample holder 6 is essentially gas and liquid impermeable.

In the case where sample holder 6 is formed from rubber gaskets, membrane and/or polymer membrane 1 is generally circular in shape. It should be noted that the present invention is not limited to just circular shaped membranes. Instead, depending upon the geometrical shape of sample holder 6, membrane 1 can be formed in suitable shape (e.g., square, rectangular, polygonal, etc.).

When membrane 1 is placed in sample holder 6, the uncovered surface of membrane and/or polymer membrane 1 in the mid-portion thereof should be much larger than the portion of membrane 1 that is held by sample holder 6. FIG. 1 also shows a concentration profile, reference numerals 3 and 4, of a penetrant in membrane 1 when the edge of membrane 1 is in contact with a penetrant having a known concentration. Reference numeral 4 represents a penetrant of concentration of $C_2$ that is the result of oxygen diffusing through the sample membrane in the directed shown by the arrows in FIG. 1. Reference numeral 3 represents a penetrant of concentration of $C_1$, concentration $C_1$ being higher than concentration $C_2$ (i.e., the concentration and/or amount of penetrant that penetrates through membrane 1 as indicated by the arrows of FIG. 1).

As discussed above, the edge effect plays a role in the detection, and even the amperometric detection, of oxygen diffusion thorough a membrane. Thus, the edge effect influences the ability of one to determine the oxygen permeability of a polymer membrane.

In light of the above, it is helpful to examine the differences that exist between the widely-used Fatt method and the method/technique of the present invention. In the Fatt method, generally used to determine the oxygen permeability of soft contact lenses, swollen concave lenses are placed on an electrode. The surfaces of the contact lenses on the electrode side and on the solution side are different and this difference produces complicated edge effects. In contrast, in the method/technique of the present invention this complex membrane/electrode interface is eliminated, and flat membranes whose surfaces are equal are analyzed. Another difference is that the membrane samples that can be measured via the present invention can be an order of magnitude larger. Consequently, such samples have larger diameter/thickness ratios than the sample commonly analyzed via the Fatt method. Due in part to the above improvements (i.e., sample position, geometry and size) the edge effect can be greatly reduce in the method/technique of the present invention.

Additionally, the present invention also involves an edge effect correction procedure. This edge effect correction procedure is achieved by computer simulation via the use of a finite element method, which is known to those of skill in the art.

Figure 2:
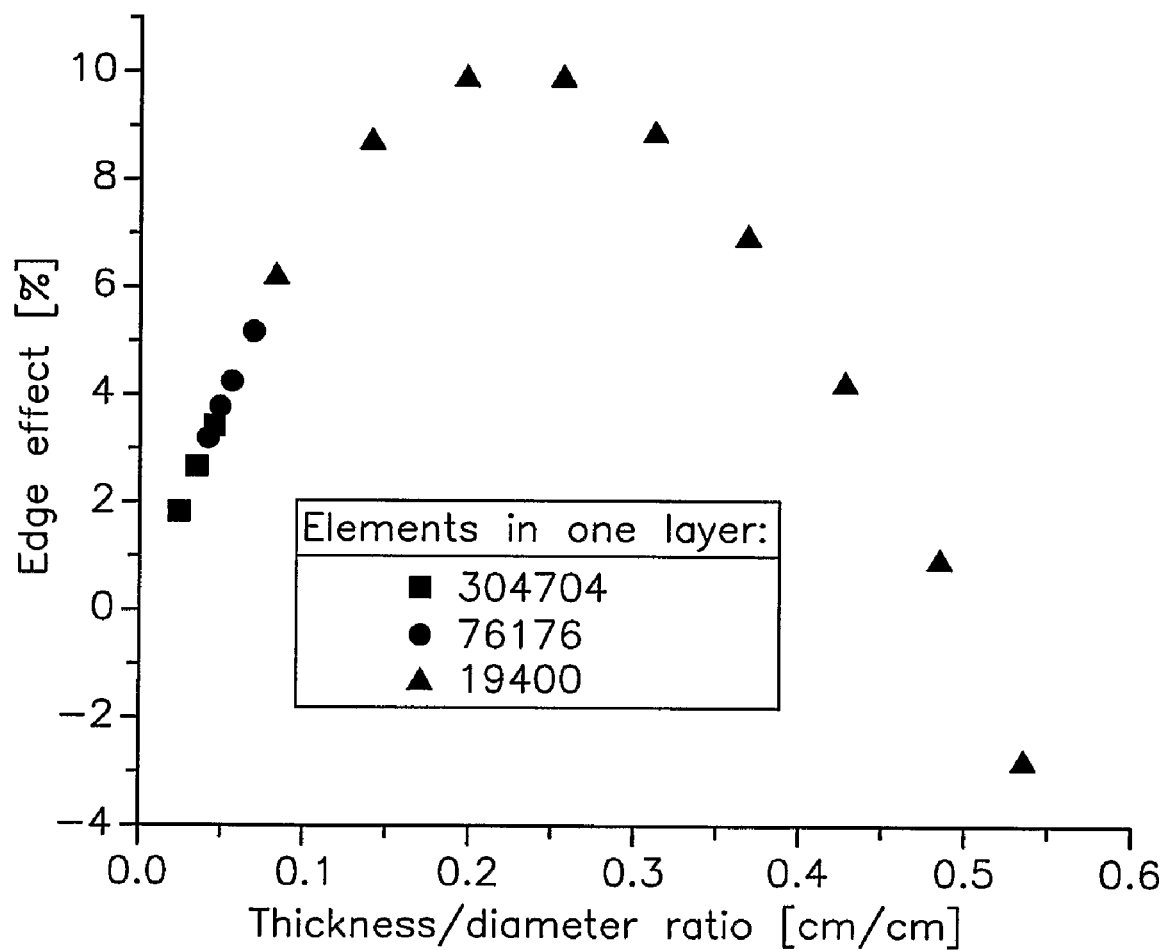
FIG. 2 is a graph illustrating an edge effect simulation in a membrane at different thickness/effective diameter ratios.

FIG. 2 is a graph illustrating the edge effects in a membrane with a total surface/effective surface equal to 3.8 as a function of thickness/diameter ratio. At a low thickness/diameter ratio (t/d) the edge effect is negligible, at a t/d equal to 0.02, the edge effect increases the apparent permeability only by 2%. At higher t/d ratios the edge effect can be 10% of the overall permeability. Above t/d equal to 0.25 the edge effect decreases because the outer edge of the membrane is in contact with a penetrant of concentration of $C_2$ (see reference numeral 4 of FIG. 1), and eventually it becomes negative due to the loss of penetrant at the outer edges. FIG. 2 contains three sets of data representing different layer sizes. Changing the layer size of the membrane was necessary to avoid slow calculations due to high cell numbers.

FIG. 2 shows that all three sets of data fit to one continuous curve indicating that the overall size of the model (the number of cells in the model) does not influence the results because the edge effect is independent of extensive parameters and of the diffusion constant. The thickness of the membrane is always more than 10 cells in the calculations, which is sufficient for the simulation of the complicated penetrant distribution functions in the membrane.

Depending on the thicknesses, the thickness/diameter (t/d) ratios of the membranes prepared and used in the experiments of the present invention are in the about 0.02 to about 0.07 range. In this range the edge effect becomes significant requiring a 2 to 5% correction of the apparent permeability. The percent edge effect at lower t/d ratios can be approximated by the following equation:

$$\text{edge effect} = 87.6[t/d] - 109.2[t/d]^2 \qquad (3)$$

Although a 2 to 5% correction is within the statistical error of the method/technique of the present invention, and could be neglected, the edge effect correction is necessary because the thickness dependency of the edge effect correction can yield up to a 10% error in the boundary layer corrected permeability.

Figure 3:
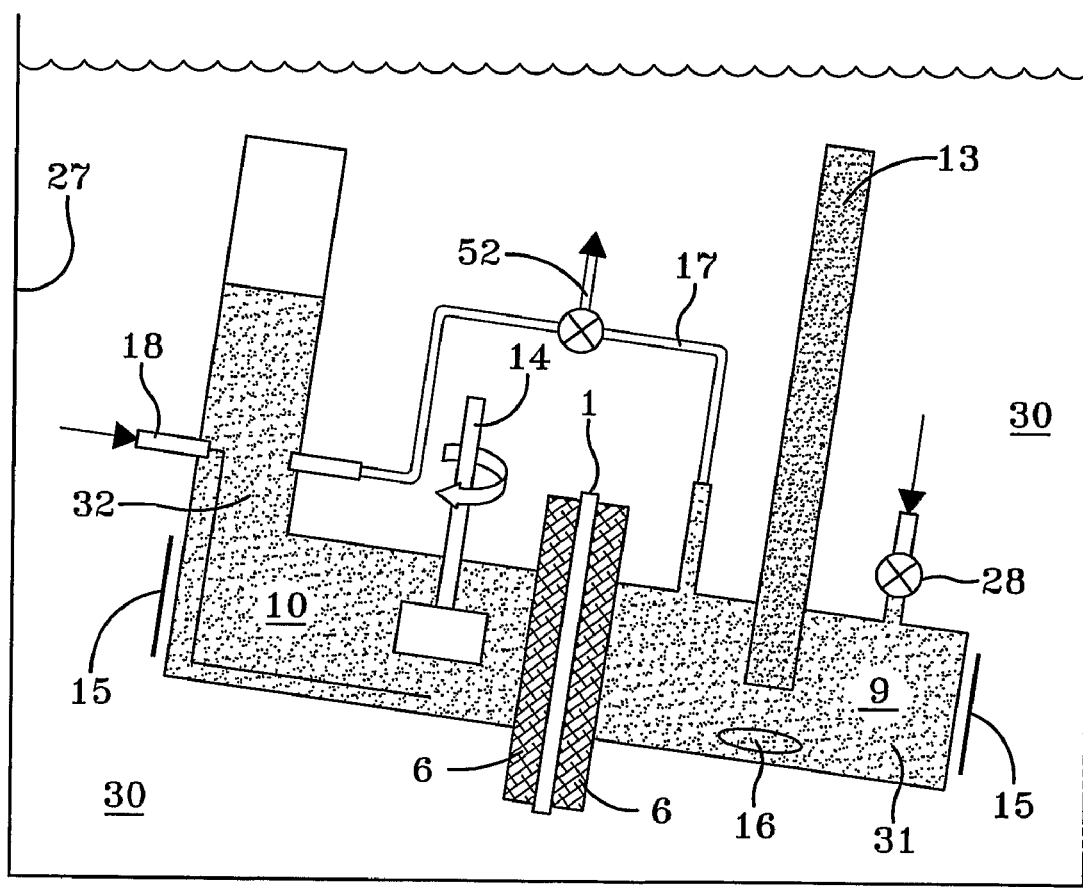
FIG. 3 illustrates a testing apparatus according to one embodiment of the present invention, the testing apparatus being designed to determine and/or measure the oxygen permeability of one or more polymer membranes in solution.
Figure 4:
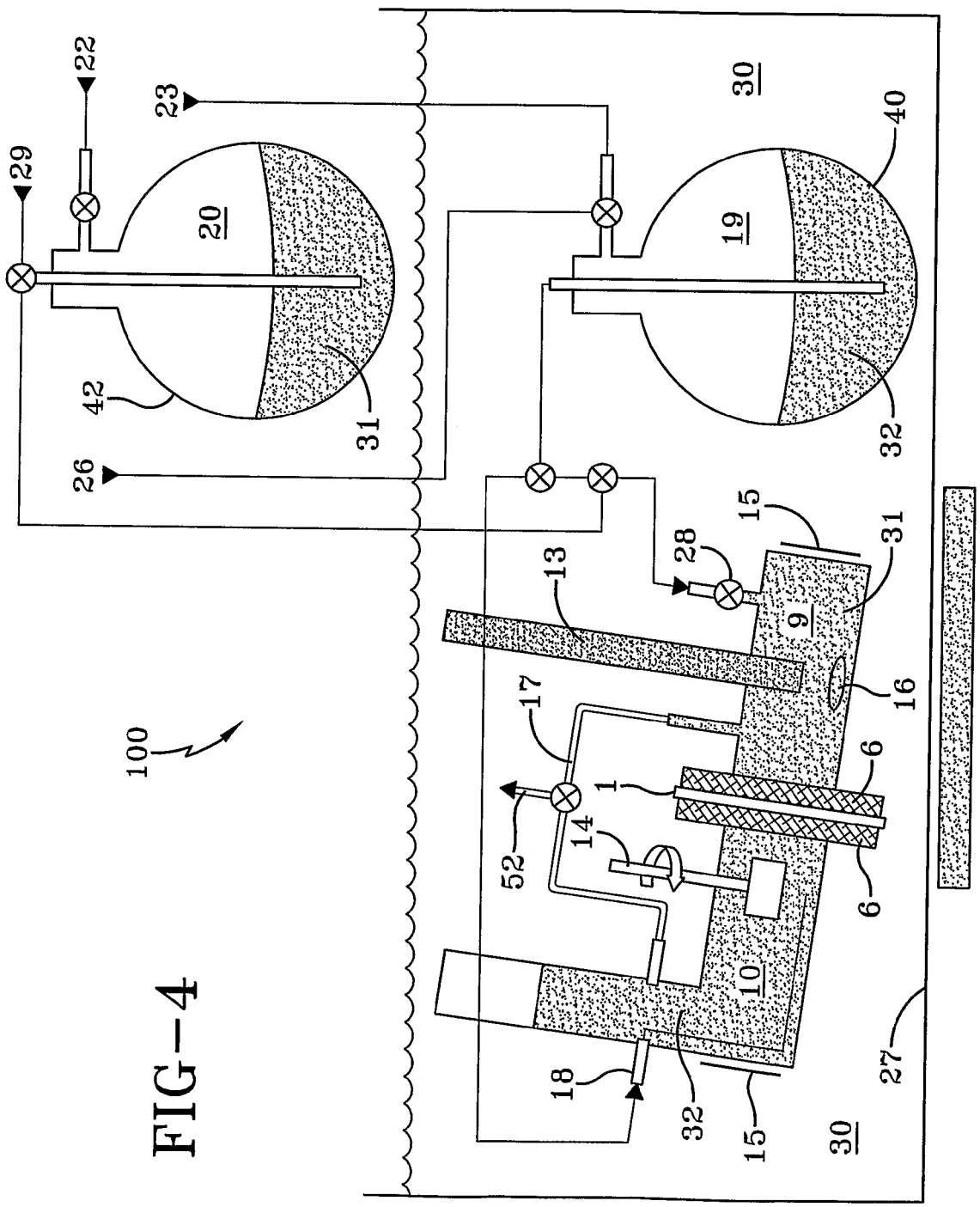
FIG. 4 illustrates a testing apparatus according to another embodiment of the present invention, FIG. 4 showing one possible set-up for supplying air and oxygen gases to the testing apparatus of FIG. 3.

Turning to FIGS. 3 and 4, a detailed discussion of an apparatus for conducting oxygen permeability measurements on membranes and/or polymer membranes, in accordance with the present invention, will be discussed. FIGS. 3 and 4 show one possible embodiment for an oxygen permeability determining apparatus. In the embodiment of FIGS. 3 and 4, the apparatus is designed to measure the oxygen permeability of wet membranes and/or polymer membranes.

As can be seen from FIGS. 3 and 4, apparatus 100 comprises an oxygen-receiving enclosure 9 that is designed to hold a gas-enriched liquid 31, the gas-enriched liquid 31 of enclosure 9 having an oxygen concentration that is monitored. In one embodiment, enclosure 9 can be designed to accommodate an increased pressure (i.e., a pressure greater than 1 atmosphere). As would be appreciated by one or skill in the art upon reading and understanding this specification, enclosure 9 can be designed to be any suitable size (e.g., having a volume of about 100 mL), and be formed from any suitable material (e.g., plastic, glass, metal, etc.).

In one embodiment, the liquid 31 can be enriched with any gas that contains a known amount of oxygen and that is not destructive and/or corrosive to membrane 1. In one embodiment, this gas can be selected from oxygen-depleted air (i.e., air that contains less than approximately 20.9% by volume oxygen), atmospheric air (i.e., air that contains approximately 20.9% by volume oxygen), or oxygen-enriched air (i.e., a gas containing more than 20.9% by volume oxygen). In another embodiment, the gas in liquid 31 is atmospheric air.

Apparatus 100 also comprises an oxygen-donating enclosure 10 that is designed to hold a gas-enriched liquid 32, the gas-enriched liquid 32 of enclosure 10 having an oxygen concentration that is greater than the oxygen concentration in enclosure 9. As with enclosure 9, enclosure 10 can also be designed to accommodate an increased pressure (i.e., a pressure greater than 1 atmosphere). As would be appreciated by one or skill in the art upon reading and understanding this specification, enclosure 10 can be designed to be any suitable size (e.g., having a volume of about 100 mL), and be formed from any suitable material (e.g., plastic, glass, metal, etc.).

In one embodiment, the liquid 32 can be enriched with any gas that contains a known amount of oxygen that is greater than the amount of oxygen in the gas used to enrich liquid 31. In one embodiment, this gas can be selected from atmospheric air, oxygen-enriched air, or pure oxygen. In another embodiment, the gas in liquid 32 is oxygen-enriched air having an oxygen content of at least 21% by volume.

In another embodiment, the oxygen concentration in liquid 31 is about 6.0±0.05 mg/L and the oxygen concentration in liquid 32 is at least 11.0 mg/L. In still another embodiment, the oxygen concentration of liquid 31 is determined and the oxygen concentration of liquid 32 is set to be at least 5.0 mg/L higher than the oxygen concentration of liquid 31. In another embodiment, the oxygen concentration of liquid 31 is determined and the oxygen concentration of liquid 32 is set to be at least 7.5 mg/L higher, or at least about 10.0 mg/L higher, or at least about 12.5 mg/L higher, or at least about 15.0 mg/L higher, or at least about 17.5 mg/L higher, or at least about 20.0 mg/L higher, or at least about 22.5 mg/L higher, or even at least about 25.0 mg/L than the oxygen concentration of liquid 31. Here, as well as elsewhere in the specification and claims, numerical values can be combined to yield ranges.

As can be seen in FIGS. 3 and 4, enclosures 9 and 10 are separated by a combination of sample holder 6 and membrane 1. Again, the size and thickness of sample holder 6 is not critical, and, as discussed above, is determined based on the size/geometry of membrane 1.

In one embodiment, membrane 1 is generally circular in shape and has a diameter of about 8 centimeters. In this case, membrane 1 is positioned over a circular opening, having a diameter of about 4.30 centimeters, in sample holder 6. Sample holder 6 is then positioned between enclosures 9 and 10 prior to the enclosures being filled with their respective liquids.

In greater detail, membrane 1 and sample holder 6 of this embodiment comprise a circular sample membrane 1 sandwiched between rubber gaskets 6 located between the enclosures 9 and 10. Also present in apparatus 100 are an oxygen sensor or electrode 13, a stirring means 14 (e.g., a mechanical or magnetic stirrer), a metal stand 15 (designed to hold enclosures 9 and 10, membrane 1, sample holder 6, and the remaining elements attached thereto stable in tank 27). As can be seen in FIG. 4, tank 27 contains water 30 for isolating enclosures 9 and 10, as well as, sample 1 therein.

Apparatus 100 also comprises a stirring means 16, (e.g., a mechanical or magnetic stirrer), located below, or near, oxygen sensor or electrode 13. Additionally, apparatus 100 includes a liquid bridge 17 between enclosures 9 and 10 (for equalizing pressure between the enclosures, or to permit a pressure bleed off via safety valve 52, if need be) and a gas inlet 18 that is connected via a suitable supply means (e.g., a pipe) to a reservoir 40 that contains liquid 32 and an oxygen-enriched gas 19, the concentration of oxygen in gas 19 being greater than the oxygen gas concentration in gas 20. Reservoir 40 also contains an inlet 23 for gas 19 and an outlet 26 to the atmosphere.

Besides permitting the equalization of any pressure difference between enclosures 9 and 10, bridge 17 also prevents distortion (bulging) of membrane 1 during testing/measurement. It should be that during oxygen gas measurement, safety valve 52 is position such that enclosures 9 and 10 are isolated from each other and any external environment (e.g., the environment of tank 27).

Continuing on, apparatus 100 contains a reservoir 42 that is connected via a suitable supply means (e.g., a pipe) to inlet 28 of enclosure 9. As can be seen from FIG. 4, reservoir 42 contains liquid 31 and a gas 20, the concentration of oxygen in gas 20 being less than the oxygen gas concentration in gas 19. Reservoir 42 also contains an inlet 22 for gas 20, and an outlet 29 to the atmosphere. In one embodiment tank 27 be temperature controlled thereby allowing for water 30 to be above or below the room temperature.

Figure 5:
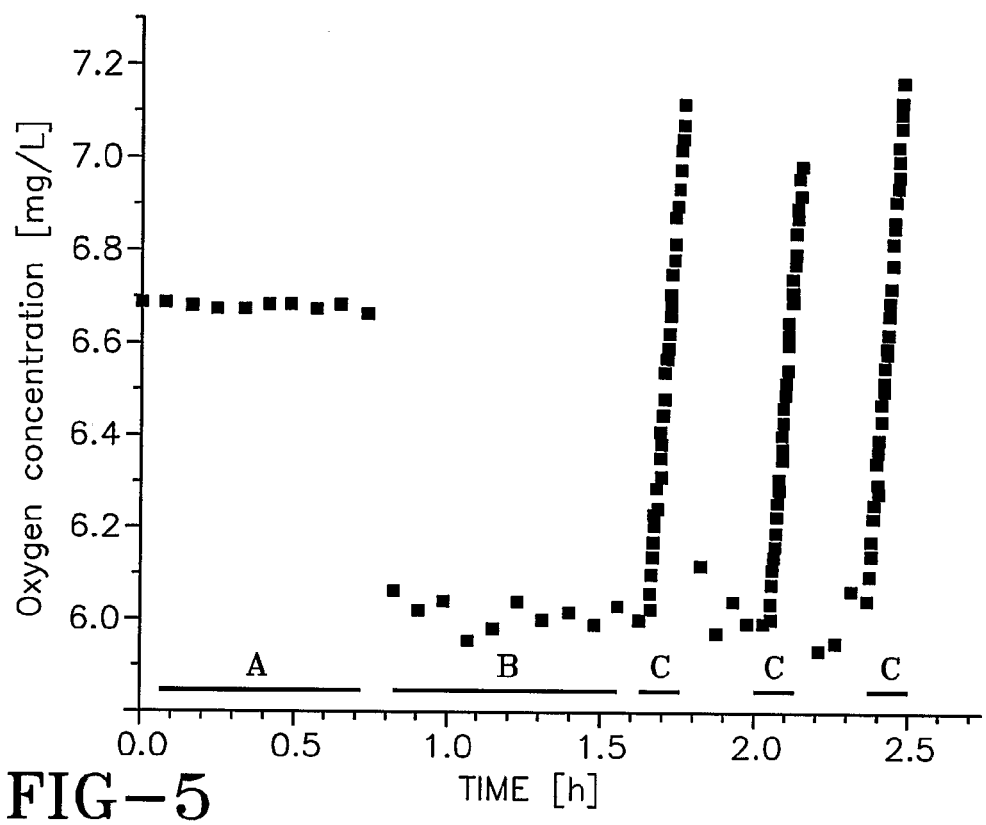
FIG. 5 is a plot of oxygen concentration profiles over time: (A) during measurement of the oxygen consumption rate of the electrode; (B) maintaining constant oxygen concentration until steady-state is reached; and (C) during permeability measurement (3 runs—sample membrane sample)

Next a method for determining the oxygen permeability of a membrane and/or polymer membrane will be described with reference, where needed to the attached Figures. In one embodiment, after apparatus 100 is assembled as discussed above, a measurement according to the present invention involves at least the following steps: (1) removing any gas bubbles, if present, in enclosure 9; (2) determining and/or measuring the oxygen consumption rate of oxygen sensor/electrode 13; (3) determining the initial oxygen concentrations in enclosures 9 and 10 (i.e., steady-state conditions; (4) measuring the amount of oxygen gas transport across/through membrane 1. FIG. 5 shows oxygen concentration profiles in enclosure 9 during steps (2) through (4). The present invention is demonstrated by determining the Dk of PDMS, two random copolymers, P(DMS-co-DES) and P(DMS-co-DPS), and a PureVision membrane. The presence of —OSiEt$_2$- and —OSiPh$_2$- repeating units leads to a reduction in the oxygen permeability of PDMS.

In one embodiment, the oxygen concentration is monitored by am amperometric oxygen sensor 13 connected to an oxygen meter that can, in one embodiment, send temperature-, pressure-, and salt-corrected oxygen concentrations to a computer. In this embodiment, the original internal stirring rod and plastic joint of the commercially bought oxygen sensor are removed and replaced by a ground glass joint to ensure hermetic sealing of the sensor 13 to the glass adapter of enclosure 9. A magnetic stirrer 16 provides agitation in enclosure 9; the stirrer 16 is positioned close to the bottom of sensor 13 to effect stirring in the vicinity of sensor 13.

The complete removal of even the tiniest air bubbles from the receiver chamber 9 is important to the accurate determination of the oxygen permeability of a membrane and/or polymer membrane in accordance with the present invention. This is because the oxygen concentration in air is approximately 30 times higher than that of air-saturated water. Thus, the presence of even a few tiny air bubbles adhering to the wall of enclosure 9 can significantly affect the present invention's results by altering the amount of oxygen in the chamber at a given pressure. Adhering air bubbles are, in one embodiment, removed by passing degassed water through the enclosure 9 for about 30 minutes prior to measurement. The degassed water dissolves and removes any air bubbles that may cause/lead to measurement errors. In this embodiment, sensor 13 is calibrated prior to conducting a measurement by passing air-saturated water 31 through enclosure 9. Water 31 is saturated with air at the known temperature of water bath 30.

The amperometric oxygen sensor 13 consumes oxygen during its operation; therefore its oxygen consumption has to be determined and taken into account. The oxygen consumption rate of the sensor 13 is in the range of 0.8 to 1.0 mg/h when the oxygen gas concentration in a liquid is in the 6.0 to 8.0 8 mg/L range, which represents 1 to 10% of the oxygen transported through membrane 1. This correction factor is quite stable, and only needs to be monitored occasionally. It should be noted that the determination of this correction factor can only be made with relatively thin membranes. Thick membranes with high oxygen solubility coefficients may absorb or release oxygen for long times before the oxygen concentration in the system reaches equilibrium; slow equilibration can render oxygen consumption rate measurements inordinately long.

Equation (1) can be applied to calculate Dk only when the concentration gradient in the membrane is stable. Thus, constant oxygen concentrations must be maintained in enclosures 9 and 10 for a sufficient length of time (e.g., at least about 10 minutes) prior to conducting a measurement.

As discussed above, prior to measurement, enclosure 10 contains an oxygen-enriched liquid 32 (e.g., water or saline), and the oxygen concentration in liquid 31 of enclosure 9 is known. In one embodiment, the oxygen concentration in liquid 31 is about 6.0 mg/L±0.05 mg/L. The oxygen-enriched liquid 32 in enclosure 10 can be obtained by bubbling a suitable gas into liquid 32 (e.g., oxygen-enriched air, or pure oxygen) under stirring. The saturation of the oxygen gas with water is necessary to avoid a temperature drop in enclosure 10 due to water evaporation. The time to reach steady-state conditions is influenced by the initial oxygen concentration in the system, diffusion constants, membrane thickness, etc. Depending on nature of membrane 1, 30 to 120 minutes of equilibration are sufficient to reach steady-state conditions. This time period is significantly longer than that suggested by the well known general rule (l2/2D, where D is diffusion constant and l is thickness). This is most likely due to edge effects.

The contents of enclosure 10 are vigorously agitated by stirrer 14 whose action significantly decreases the boundary layer on the membrane 1. Rapid stirring ensures that the oxygen being supplied to enclosure 10, during measurement, dissolves significantly faster than that transported to enclosure 9. Since stirring strongly influences the boundary layers, the rate of stirring should be constant (e.g., 1,000±10 rpm). Also, the position of stirrer 14, gas inlet 18, and the overall geometry of the chamber should remain the same in every measurement to help ensure the same boundary layer conditions on the different membranes/samples. The enclosure/sample holder/membrane assembly is, in one embodiment, tilted approximately 80 from horizontal to avoid the deposition of bubbles on the surface of the membrane 1. It should be noted that the present invention is not limited to any one angle of tilt. Rather, any suitable angle can be used, as would be appreciated by one of skill in the art.

During measurement, enclosure 9 is closed and the oxygen concentration therein is constantly monitored by sensor 13 as the oxygen concentration increases by about 0.5 to about 1.0 mg/L over the initial oxygen concentration in enclosure 9 (approximately 6.0 mg/L). In this embodiment, the oxygen concentration in enclosure 9 is approximately 6.0 mg/L and in enclosure 10 is approximately 32 mg/L. This is due to the fact that the following gases are used in this embodiment to provide the gases needed to produce gas-enriched liquids 31 and 32—air containing 20.9±0.1% oxygen (balance nitrogen—obtained from Praxair) and oxygen gas (99.999% pure—obtained from Praxair), respectively. This increase is only 2 to 4% of the oxygen concentration difference between the two chambers. Although a longer time would increase the precision of the measurement, under such circumstances the deviation from steady-state conditions can become significant.

The apparent oxygen permeability is measured 3 to 5 times in every experiment and the values averaged. Prior to further measurements, the oxygen concentration is maintained constant in enclosure 9 for 15 to 30 minutes. The relative standard error of the apparent permeability calculated from repeat measurements was ±1.0 to ±2.5%. This shows that the experimental conditions, especially the boundary layer effect, are constant during the measurement.

The measurement of the oxygen consumption rate of sensor 13 in enclosure 9 is calculated by fitting a linear equation to the initial part of the experimental concentration/time plot.

The correction factor is expressed as the rate of oxygen concentration decrease in the chamber in mg/L-h.

Equation (4) shows the integrated form of Equation (1) together with the oxygen consumption rate of the electrode:

$$C = \left(C_0 - \frac{EC}{a}\right)(1 - e^{-a(t-t0)}) \quad (4)$$

Where $C_O$ is equal to $C_{air}/0.2094$ (mg/L) and is the oxygen concentration of oxygen-saturated water (calculated from the calibration constant of the electrode: $C_{air}$, which is the oxygen concentration of air-saturated water (mg/L)) and the oxygen content of air (0.2094), EC is the oxygen consumption rate of the electrode (mg/L-h), t is time (in hours) and t0 is the initial parameter of time (also in hours). Parameter a contains the apparent permeability of the sample, together with other constants:

$$a = \frac{3.6 \times 10^{13} A d K}{l V_c} Dk' \quad (5)$$

where A is the area of the sample (cm²), d is the density of oxygen at STP (1.429 mg/cm³), l is the thickness of the sample (cm), $V_c$ is the volume of the receiving enclosure/chamber (e.g., 89.7 cm³) and K is the solubility constant of oxygen in water according to Henry's law at the temperature and pressure of the experiment. K is calculated by:

$$K = \frac{0.2094(p - p_w)}{C_{air}} \quad (6)$$

where p (cm Hg) is the barometric pressure during experiment and $p_w$, (cm Hg) is the vapor pressure of water. Since the medium of the measurement is water, $p_w$ must be subtracted from the atmospheric pressure (p–(cm Hg)). The vapor pressure of water is calculated at a given temperature (T-° C.) by:

$$p_w = 0.00075 \times 10^{(10.09 - \frac{1668}{228+T})} \quad (7)$$

In the calculation of the apparent permeability Dk', Equation (4) is fitted to concentration-time data pairs. Parameters $C^O$ and EC are fixed at their calculated values during fitting and only t0 and a are allowed to change. Dk' is calculated from parameter a by Equation (5). The standard error of Dk' is calculated from the individual measurements.

Edge effect corrected permeabilities are calculated by:

$$Dk'' = [(1 - 0.3481(l) + 0.1724(l^2))] \cdot (Dk') \quad (8)$$

where l is thickness (cm) and Dk' is the apparent permeability in barrers.

Equation (9) shows the edge effect corrected inverse transmissibility as a function of membrane thickness.

$$\frac{l}{Dk''} = \frac{l}{Dk} + \frac{l_b}{Dk_b} \quad (9)$$

Permeability Dk is calculated from the reciprocal slopes of linear plots of inverse transmissibility/thickness data pairs.

The applicability of this methodology is demonstrated by determining the oxygen permeability of four membranes. Two membranes of known high oxygen permeabilities, and two membranes that are expected to have high oxygen permeabilities. Of the four membranes, three are prepared, with the fourth being "PureVision", available from Bausch and Lomb Co. While the composition/structure of the PureVision sample is an unknown, the sample's oxygen permeability—Dk equal to 90 barrer—is known and was provided by the manufacturer.

Of the three prepared membranes, one is a crosslinked essentially pure PDMS membrane (with —OSiMe₂— repeating units), while the other two are crosslinked random copolymers of —OSiMe₂-/—OSiEt₂- and —OSiMe₂-/—OSiPh₂-repeating units. The conventional names and abbreviations of these three polymers are polydimethylsiloxane PDMS; poly(dimethylsiloxane-codiethylsiloxane) P(DMS-co-DES) 80/20; and poly(dimethylsiloxane-co-diphenylsiloxane) P(DMS-co-DPS) 84/16; the ratios indicate the molar ratios of the respective repeating units in the copolymers.

The membranes are prepared by hydrosilating vinyl-telechelic polymer segments with the three-functional cross-linking agent tris(dimethylsilyloxy)phenylsilane t(DS)PS, in the presence of an efficient Pt-based hydrosilating catalyst (see Scheme 1).

Scheme 1 - Crosslinking by Hydosilation of Siloxane Polymers

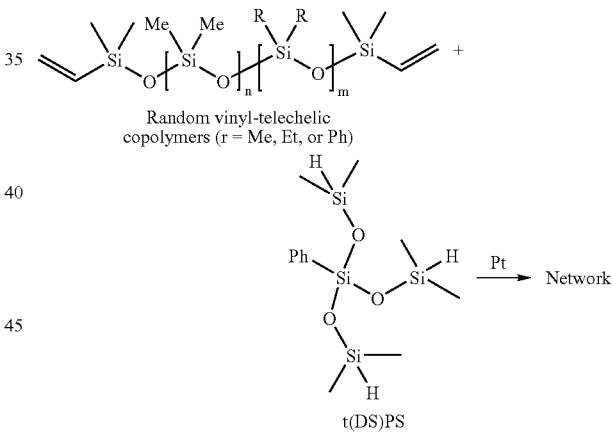

End-to-end cross-linking is very sensitive to the exact stoichiometry of the reactants and the precise knowledge of relative molar concentrations of the reagents is mandatory. The exact stoichiometry for the synthesis of the PDMS network can be calculated because accurate molecular weights are available for the vinyl-telechelic PDMS starting material. In contrast, the stoichiometry for the synthesis of the other two networks can not be calculated because sufficiently accurate molecular weights for vinyl-telechelic P(DMS-co-DES) and P(DMS-co-DPS) are unavailable (the Gelest catalogue lists only a wide molecular weight range for these products). Thus, the appropriate cross-linking stoichiometry is determined empirically. Accordingly, a series of networks with different P(DMS-co-DES)/t(DS)PS and P(DMS-co-DPS)/t(DS)PS ratios are prepared, and the sol content of the networks are determined quantitatively by extraction with THF.

Reactant ratios that gave minimum sol (<8%), i.e., the highest crosslink density, are employed in subsequent network synthesis for permeability investigations.

The molecular weights of the polymers are similar (9,000 to 15,000 g/mol) so their permeabilities are comparable. The membranes did not contain silica or other additives.

Figure 6:
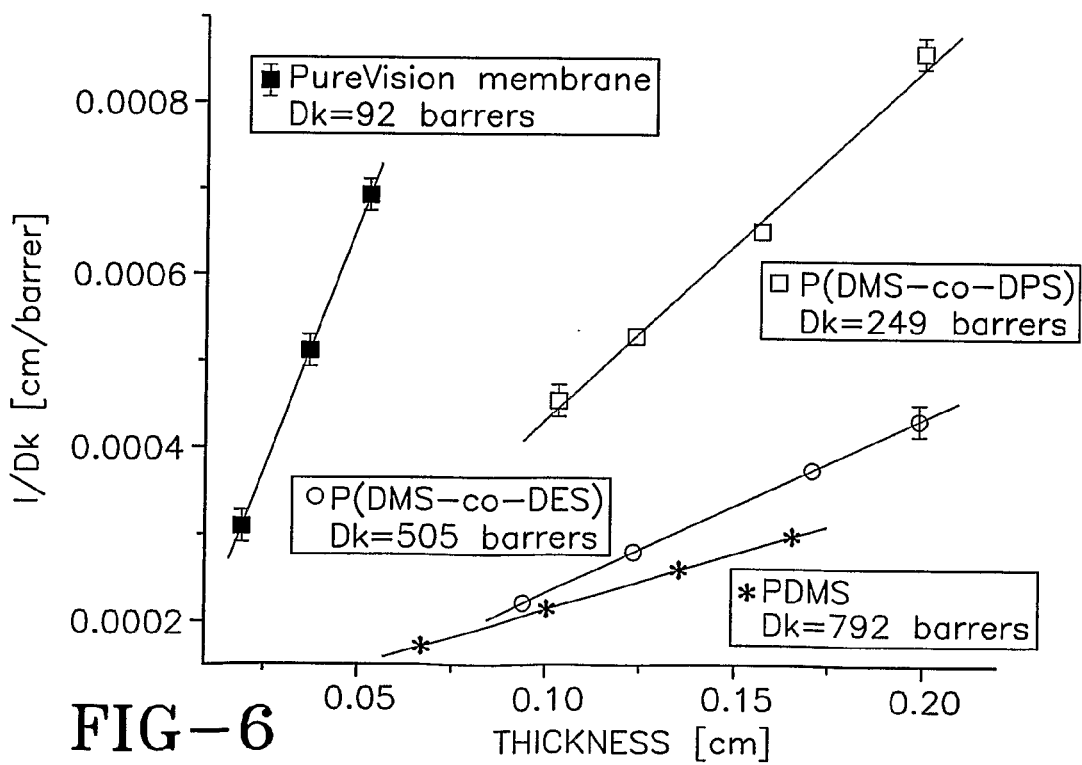
FIG. 6 is a plot of the oxygen permeabilities of various membranes at varying thicknesses.

As indicated by Equations (2) and (8), the oxygen permeability, Dk, of a membrane can be obtained from the slope of a linear plot of inverse transmissibility l/Dk versus membrane thickness l. Accordingly, membranes are prepared from each composition with different (at least three) thicknesses in the 0.6 to 2.0 mm range, and their l/Dk values are determined. The thicknesses of the PureVision membranes are 0.188, 0.381 and 0.538 mm. Since the latter membranes are pH sensitive, their oxygen permeability is determined by the use of buffered (pH equal to 7.0) isotonic (0.95%) saline. FIG. 6 is a graph illustrating the oxygen permeability of various membranes and shows the edge effect corrected inverse transmissibility plot of the samples as a function of membrane thickness l. The plots show linear relationships between inverse transmissibilities and membrane thicknesses, i.e., the results indicate excellent agreement with theory.

Table 1 shows the permeabilities of the siloxane polymers examined. The oxygen permeability of PDMS determined by the technique of the present invention is in good agreement with permeability values measured by others via dry methods. The Dk obtained herein for PDMS, 792±26 barrers, is significantly higher than the often quoted range of 200 to 600 barrers for "wet siloxane". Since PDMS is highly hydrophobic, the presence of water is not expected to affect its oxygen permeability.

TABLE 1

Permeability of Siloxane Polymers

| Sample | Permeability [barrer[a]] | Literature values [barrer[a]] |
|---|---|---|
| PDMS | 792 ± 26 | 781[b], 820[b], 800[b] |
| P(DMS-co-DES) | 505 ± 12 | — |
| P(DMS-co-DPS) | 249 ± 10 | — |
| PureVision membrane | 92 ± 4 | 90[c] |

[a]barrer = ($10^{10}$ cm$^3$ (STP) cm/s cm$^2$ cm Hg)
[b]dry membrane measured by isostatic methods
[c]water-swollen membrane measured by the Fatt method Table 2 shows the reagents and amounts used for the synthesis of networks.

TABLE 2

| | Polymer (g) | t(DM)PS (mg) | Pt Catalyst (μL) |
|---|---|---|---|
| PDMS | 10.0 | 267 | 5.0 |
| P(DMS-co-DES) | 10.0 | 278 | 5.0 |
| P(DMS-co-DPS) | 10.0 | 262 | 5.0 |

It is of interest that the P(DMS-co-DES) and P(DSM-co-DPS) membranes exhibit much lower oxygen permeabilities than PDMS in spite of the great structural similarity of the polymers. In P(DMS-co-DES), Dk equal to 505±12 barrers, the presence of 25% weight fraction of —OSiEt$_2$— units decreases the Dk of this polymer by 35% relative to pure PDMS. The Dk of this copolymer is somewhat lower than expected from the weight fraction of the components assuming that the permeability of PDES is not higher than that of poly(methylethylsiloxane), approximately 312 barrers. In regard to P(DMS-co-DES), Dk equal to 249±10 barrers, the presence of 33% weight fraction of —OSiPh$_2$- units decreases the Dk by approximately 70% relative to PDMS. This decrease is much larger than calculated from the —OSiPh$_2$-/—OSiMe$_2$- ratio in this copolymer and assuming that the Dk for PDPS is lower than 32 barrers found for poly(methylphenylsiloxane).

While not wishing to be bound to any one theory, the lowered Dk's of the copolymers may be partly due to a decreased diffusion constant of the Et and Ph substituents, and partly to a restriction in the mobility of —OSiMe$_2$- units by these substituents. Overall, the oxygen permeability will be significantly reduced because long contiguous —OSiMe$_2$- sequences are absent in these copolymers. Evidently, these effects are more pronounced in the presence of the relatively rigid —OSiPh$_2$-units than with the more flexible —OSiEt$_2$-groups.

The oxygen permeability of the PureVision membrane is determined to be Dk equal to 92±4 barrer, almost identical to the value determined by Bausch and Lomb scientists via the Fatt method.

The standard error of apparent permeabilities calculated from individual data obtained in an experiment (n is equal to 3 to 5) is 0.5 to 2.5% (RSD). The relative standard error of oxygen permeabilities is about 2 to about 4% which indicates excellent reproducibility. By taking into consideration the sources of other errors [i.e., ±0.5% relative error of oxygen concentration (±0.1% claimed by the manufacturer of the oxygenmeter); ±5 μm error of thickness measurement (measured by a micrometer); 0.1° C. error of temperature measurement; ±1.0% relative error of the oxygen content of air; and ±11% relative error of the oxygen consumption rate of the electrode (SD)], the relative error increases to about 5 to about 8%. However, even this error range is quite satisfactory and acceptable, particularly in comparison with the errors reported by others.

An Accumet AR40 Oxygenmeter is used to determine oxygen concentrations. Vinyl-telechelic polydimethylsiloxane (PDMS) ($M_W$=9,000 g/mol), vinyl-telechelic poly (dimethylsiloxane-co-diethylsiloxane) P(DMS-co-DES) ($M_W$=16,000 g/mol, 80:20 molar ratio); poly(dimethylsiloxane-co-diphenylsiloxane) P(DMS-co-DPS) ($M_W$=9,000 g/mol, 84/16 molar ratio), tris(dimethylsilyloxy)phenylsilane (t(DM)PS) and the platinum carbonyl cyclovinylmethylsiloxane complex (2% platinum concentration in vinylmethylcyclosiloxanes) are available from Gelest. Oxygen gas (99.999%) and air containing 20.9±0.1% oxygen, balance nitrogen, are obtained from Praxair. The glass plates are obtained from Chemglass, and the adhesive Teflon tape from VWR.

Membranes for oxygen permeability studies are prepared by the following procedure: charges containing precise stoichiometric quantities of the starting materials are placed in a 10 mL vial, the Pt catalyst is added and the mixture is stirred for about 5 minutes. Table 2 specifies the amounts of reagents employed. The clear homogeneous charges are poured into the cavities of glass/Teflon molds. The molds are prepared by creating rectangular cavities (6×6 cm) on clear glass plates, by depositing several layers (4, 6, 8, 10 or 12) of Teflon tape. The thickness of the membranes is controlled by the depth of the cavities, adjusted by piling a desired number of tapes on top of each other. The thickness of the samples is determined by a micrometer. After the cavities are filled to the brim with the charges and after all the bubbles disappear from the charges in the mold (about 5 minutes), the molds are capped with a second glass plate and the sandwich secured with sturdy steel clips. The assembly is placed in a heating oven for curing (80° C., 3 hours). At this point the membranes are visually inspected for the absence of bubbles, further heated at 80° C. for 2 days in a vacuum. The membranes so prepared are optically clear, transparent, and bubble-free with smooth surfaces. Some membranes are faintly yellow due to Pt catalyst residues. Finally, prior to oxygen permeability studies, the membranes are placed in distilled water for at least one day.

A representative measurement of oxygen permeability is carried out as follows: membrane sample 1 is placed between two rubber gaskets of sample holder 6, the sample holder 6 being located between enclosures 9 and 10. Next, enclosures 9 and 10 are gently pushed together to hermetically seal the membrane/gasket combination. Enclosures 9 and 10 are filled with distilled water, the attachments are connected to enclosures 9 and 10, and the equipment is placed in a thermostat controlled water bath 27 at 35° C. (+0.05° C.). Two liters of degassed water are prepared by stirring water in a round bottom flask under vacuum for 30 minutes. Enclosures 9 and 10 are flushed with degassed water until the oxygen concentration in receiving enclosure 9 drops below about 2.0 mg/L, or below about 1.0 mg/L, or below about 0.5 mg/L, or even below 0.25 mg/L. The water in receiving enclosure 9 is stirred for half an hour, or until all the bubbles disappear from the enclosure 9.

Two liters of air-saturated water are prepared by bubbling air for half an hour in a round bottom flask placed in the water bath. The air-saturated water is pumped into receiving enclosure 9. As the air-saturated water starts to fill the enclosure the oxygen concentration increases. In the meantime, water-saturated air is bubbled in donating enclosure 10. Oxygen sensor 13 is calibrated to air when the reading on the oxygen meter stops increasing. Receiving enclosure receiving enclosure 9 is then sealed, and the oxygen concentration in receiving enclosure 9 is monitored for two hours to obtain the rate of oxygen consumption.

Oxygen-saturated water is bubbled into donating enclosure 10 at 10 mL/min and degassed water is flushed through receiving enclosure 9 at a such rate that the oxygen concentration in receiving enclosure 9 remained constant at 6.0±0.05 mg/L. This procedure is continued for about 30 to 120 minutes depending on the thickness and expected permeability of membrane 1. Subsequently, receiving enclosure 9 is closed and the oxygen concentration is monitored until it increased by about 0.5 to 1.0 mg/L. Next, receiving enclosure 9 is flushed with degassed water for about 15 to 60 minutes at such a rate that the oxygen concentration in receiving enclosure 9 remained constant at 6.0±0.05 mg/L. This procedure is repeated 3 to 5 times.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. An apparatus for measuring the oxygen gas permeability of a polymer membrane, the apparatus comprising:
   (a) an oxygen-donating enclosure, where the oxygen-donating enclosure is designed to hold a first gas-enriched liquid, and where the first gas-enriched liquid has a first oxygen gas concentration;
   (b) an oxygen-receiving enclosure operatively coupled to the oxygen-donating enclosure, where the oxygen-receiving chamber is designed to hold a second gas-enriched liquid, and where the second gas-enriched liquid has a second oxygen gas concentration, the second oxygen gas concentration being at least about 5.0 mg/L less than the first oxygen gas concentration;
   (c) a polymer membrane holding means designed to hold and receive a polymer, where the polymer membrane holding means is in both fluid communication and direct contact with both the oxygen-receiving enclosure and the oxygen-donating enclosure, where the polymer membrane holding is being designed to prevent liquid mixing of the first and second gas-enriched liquids when a polymer membrane is present in the polymer membrane holding means;
   (d) a sensor means, where the sensor means is located in and monitors the oxygen level present in the oxygen-receiving enclosure;
   (e) a means for determining/measuring the oxygen gas transport across the polymer membrane using data from (d) and generating oxygen gas transport data therefrom; and
   (f) a means for determining the oxygen gas permeability of the polymer membrane, where the means for determining the oxygen gas permeability of the polymer membrane involves using the oxygen gas transport data from (e) to determine the oxygen permeability of the polymer membrane.

2. The apparatus of claim 1, wherein the first gas-enriched liquid is an air-enriched liquid.

3. The apparatus of claim 1, wherein the first gas-enriched liquid has an oxygen gas concentration of about 6.0 mg/L.

4. The apparatus of claim 1, wherein the second gas-enriched liquid is enriched with a gas selected from oxygen gas, oxygen-enriched air, or an oxygen-containing gas where the amount of oxygen in the oxygen-enriched air or the oxygen-containing gas is at least about 21% by volume oxygen.

5. The apparatus of claim 1, wherein the second gas-enriched liquid has an oxygen gas concentration of about 6.05 mg/L.

6. The apparatus of claim 1, wherein the first gas-enriched liquid and second gas-enriched liquid are independently selected from water or saline.

7. The apparatus of claim 1, wherein the sensor means is an amperometic oxygen sensor.

8. The apparatus of claim 1, wherein the sensor means also monitors the temperature and salt concentration of the second gas-enriched liquid in the oxygen-receiving enclosure.

9. The apparatus of claim 1, further comprising independent agitation means in the oxygen-donating and the oxygen-receiving enclosures for agitating the first and second gas-enriched liquids.

10. The apparatus of claim 1, further comprising a means for independently removing impurities from either one or both of first and second gas-enriched liquids.

11. The apparatus of claim 10, wherein the means for independently removing impurities from either one or both of first and second gas-enriched liquids comprises a means for passing degassed water or saline through one or both of the oxygen-donating and oxygen-receiving enclosures.

12. The apparatus of claim 1, wherein the polymer membrane is a contact lens.

13. The apparatus of claim 1, wherein the polymer membrane is a hydrogel membrane.

14. The apparatus of claim 1, wherein the polymer membrane is formed from a polydimethylsiloxane polymer.

15. The apparatus of claim 1, wherein the polymer membrane is formed from a polysiloxane polymer or copolymer.

16. The apparatus of claim 1, wherein the apparatus is capable of measuring an oxygen permeability value in the range of about 50 and about 5000 barrers.

17. The apparatus of claim 16, wherein the apparatus is capable of measuring an oxygen permeability value in the range of about 100 and about 1000 barrers.

18. The apparatus of claim 16, wherein the apparatus is capable of measuring an oxygen permeability value in the range of about 400 and about 900 barrers.

19. The apparatus of claim 1, wherein the apparatus is capable of measuring an oxygen permeability value in the range of about 100 and about 400 barrers.

20. The apparatus of claim 1, wherein the apparatus utilizes, in part, Fick's second law to determine the oxygen gas permeability of the polymer membrane.

21. A method for determining the oxygen gas permeability of a polymer membrane, the method comprising the steps of:
   (1) placing a polymer membrane to be tested in a device comprising:
      (a) an oxygen-donating enclosure, where the oxygen-donating enclosure is designed to hold a first gas-enriched liquid, and where the first gas-enriched liquid has a first oxygen gas concentration;
      (b) an oxygen-receiving enclosure operatively coupled to the oxygen-donating enclosure, where the oxygen-receiving chamber is designed to hold a second gas-enriched liquid, and where the second gas-enriched liquid has a second oxygen gas concentration, the second oxygen gas concentration being at least about 5.0 mg/L less than the first oxygen gas concentration;
      (c) a polymer membrane holding means designed to hold and receive a polymer, where the polymer membrane holding means is in both fluid communication and direct contact with both the oxygen-receiving enclosure and the oxygen-donating enclosure, where the polymer membrane holding is being designed to prevent liquid mixing of the first and second gas-enriched liquids when a polymer membrane is present in the polymer membrane holding means;
      (d) a sensor means, where the sensor means is located in and monitors the oxygen level present in the oxygen-receiving enclosure;
      (e) a means for determining/measuring the oxygen gas transport across the polymer membrane using data from (d) and generating oxygen gas transport data therefrom; and
      (f) a means for determining the oxygen gas permeability of the polymer membrane, where the means for determining the oxygen gas permeability of the polymer membrane involves using the oxygen gas transport data from (e) to determine the oxygen permeability of the polymer membrane;
   (2) removing any gas bubbles, if present, in the oxygen-receiving enclosure;
   (3) determining and/or measuring the oxygen consumption rate of the sensor means;
   (4) determining the initial oxygen concentrations in the oxygen-donating and oxygen-receiving enclosure; and
   (5) measuring the amount of oxygen gas transport across/through the polymer membrane.

22. The method of claim 21, wherein the first gas-enriched liquid is an air-enriched liquid.

23. The method of claim 21, wherein the first gas-enriched liquid has an oxygen gas concentration of about 6.0 mg/L.

24. The method of claim 21, wherein the second gas-enriched liquid is enriched with a gas selected from oxygen gas, oxygen-enriched air, or an oxygen-containing gas where the amount of oxygen in the oxygen-enriched air or the oxygen-containing gas is at least about 21% by volume oxygen.

25. The method of claim 21, wherein the second gas-enriched liquid has an oxygen gas concentration of about 6.05 mg/L.

26. The method of claim 21, wherein the first gas-enriched liquid and second gas-enriched liquid are independently selected from water or saline.

27. The method of claim 21, wherein the sensor means is an amperometic oxygen sensor.

28. The method of claim 21, wherein the sensor means also monitors the temperature and salt concentration of the second gas-enriched liquid in the oxygen-receiving enclosure.

29. The method of claim 21, further comprising independent agitation means in the oxygen-donating and the oxygen-receiving enclosures for agitating the first and second gas-enriched liquids.

30. The method of claim 21, further comprising a means for independently removing impurities from either one or both of first and second gas-enriched liquids.

31. The method of claim 30, wherein the means for independently removing impurities from either one or both of first and second gas-enriched liquids comprises a means for passing degassed water or saline through one or both of the oxygen-donating and oxygen-receiving enclosures.

32. The method of claim 21, wherein the polymer membrane is a contact lens.

33. The method of claim 21, wherein the polymer membrane is a hydrogel membrane.

34. The method of claim 21, wherein the polymer membrane is formed from a polydimethylsiloxane polymer.

35. The method of claim 21, wherein the polymer membrane is formed from a polysiloxane polymer or copolymer.

36. The method of claim 21, wherein the apparatus is capable of measuring an oxygen permeability value in the range of about 50 and about 5000 barrers.

37. The method of claim 36, wherein the apparatus is capable of measuring an oxygen permeability value in the range of about 100 and about 1000 barrers.

38. The method of claim 36, wherein the apparatus is capable of measuring an oxygen permeability value in the range of about 400 and about 900 barrers.

39. The method of claim 21, wherein the apparatus is capable of measuring an oxygen permeability value in the range of about 100 and about 400 barrers.

40. The method of claim 21, wherein the Step (5) utilizes, in part, Fick's second law to determine the oxygen gas permeability of the polymer membrane.

* * * * *